(12) United States Patent
Burns et al.

(10) Patent No.: US 12,370,053 B2
(45) Date of Patent: Jul. 29, 2025

(54) SYSTEMS AND METHODS FOR SURGICAL IMPLANT GUIDANCE AND POSITIONING WITH OPTICAL SURFACE IMAGING

(71) Applicant: Sunnybrook Research Institute, Toronto (CA)

(72) Inventors: David M. Burns, Toronto (CA); Cari M. Whyne, Toronto (CA); Normand Robert, Toronto (CA)

(73) Assignee: Sunnybrook Research Institute, Toronto (CA)

( * ) Notice: Subject to any disclaimer, the term of this patent is extended or adjusted under 35 U.S.C. 154(b) by 384 days.

(21) Appl. No.: 17/832,134

(22) Filed: Jun. 3, 2022

(65) Prior Publication Data
US 2022/0296382 A1  Sep. 22, 2022

Related U.S. Application Data

(62) Division of application No. 16/562,679, filed on Sep. 6, 2019, now Pat. No. 11,589,997.

(60) Provisional application No. 62/728,256, filed on Sep. 7, 2018.

(51) Int. Cl.
*A61B 34/20* (2016.01)
*A61B 17/17* (2006.01)
*A61B 34/10* (2016.01)
*A61F 2/40* (2006.01)
*A61F 2/46* (2006.01)
*A61B 90/00* (2016.01)

(52) U.S. Cl.
CPC ........ *A61F 2/4081* (2013.01); *A61B 17/1778* (2016.11); *A61B 34/10* (2016.02); *A61B 34/20* (2016.02); *A61F 2/4612* (2013.01); *A61B 2034/107* (2016.02); *A61B 2034/2055* (2016.02); *A61B 2090/3916* (2016.02); *A61B 2090/3937* (2016.02); *A61F 2002/4632* (2013.01)

(58) Field of Classification Search
CPC .................. A61F 2/4081; A61F 2/4612; A61F 2002/4632; A61B 17/1778; A61B 34/10; A61B 34/20; A61B 2034/107; A61B 2034/2055; A61B 2090/3916; A61B 2090/3937; A61B 2017/0023; A61B 90/39; A61B 2034/105; A61B 2034/2065; A61B 2090/3983
See application file for complete search history.

(56) References Cited

U.S. PATENT DOCUMENTS

| | | |
|---|---|---|
| 3,460,537 A | 8/1969 | Zeis |
| 6,159,221 A | 12/2000 | Chakeres |
| 6,419,680 B1 | 7/2002 | Cosman |
| 8,617,180 B2 | 12/2013 | Thiran |
| 9,237,931 B2 | 1/2016 | Gowda |
| 9,408,627 B2 | 8/2016 | Sahni |

(Continued)

FOREIGN PATENT DOCUMENTS

EP    1510182 A2    3/2005

*Primary Examiner* — Joel Lamprecht
(74) *Attorney, Agent, or Firm* — Quarles & Brady LLP

(57) ABSTRACT

Described here are systems and methods for positioning a surgical implant, such as a glenoid component, or other medical device intra-operatively. In general, the systems and methods described in the present disclosure implement a computer vision system, which may be a structured light computer vision system, together with a suitable optical tracker as an accurate intra-operative tool for predicting post-operative implant position in surgical procedures.

7 Claims, 8 Drawing Sheets

(56) References Cited

U.S. PATENT DOCUMENTS 9,901,409 B2 2/2018 Yang
2005/0049486 A1 3/2005 Urquhart
2015/0202011 A1 7/2015 Gowda

SYSTEMS AND METHODS FOR SURGICAL IMPLANT GUIDANCE AND POSITIONING WITH OPTICAL SURFACE IMAGING

CROSS-REFERENCE TO RELATED APPLICATIONS

This application is a divisional of U.S. patent application Ser. No. 16/562,679, filed Sep. 6, 2019, which claims the benefit of U.S. Provisional Patent Application Ser. No. 62/728,256, filed on Sep. 7, 2018, and entitled "SYSTEMS AND METHODS FOR SURGICAL IMPLANT GUIDANCE AND POSITIONING WITH OPTICAL SURFACE IMAGING," the contents of each are incorporated herein by reference in their entireties.

BACKGROUND

Glenoid component position is an important factor for postoperative function and long-term implant survival in both anatomic and reverse total shoulder arthroplasty. For instance, glenoid component position effects shoulder motion, impingement points, and stresses at the bone-prosthesis interface. Glenoid component failure is one of the most common complications of total shoulder arthroplasty, and malposition of the glenoid component has been associated with instability, implant, loosening, early failure, and inferior clinical outcomes.

Achieving adequate alignment and stable fixation of the glenoid component can be technically challenging. Restricted visualization, limited bony landmarks, and the complex and variable scapular geometry make glenoid component placement a relatively blind procedure. Abnormal glenoid morphology and bone loss is common in primary and revision procedures, which further complicates positioning the baseplate along the anatomic centerline and achieving stable fixation.

Current orthopedic intra-operative imaging systems generally include two-dimensional (2D) and three-dimensional (3D) C-arm x-ray fluoroscopy and cone beam CT systems. Two-dimensional x-ray images do not characterize the 3D position of the glenoid component with sufficient accuracy. Intra-operative 3D x-ray imaging systems present a logistical challenge and are unwieldy for imaging the shoulder of a patient in the standard beach chair position for shoulder arthroplasty. Thus, there remains a need to provide means for verifying the position of the glenoid component intra-operatively.

SUMMARY OF THE DISCLOSURE

The present disclosure addresses the aforementioned drawbacks by providing methods for guiding a placement of a surgical implant or surgical tool. The methods include providing to a computer system, one or more pre-operative images that depict a patient and an anatomical region-of-interest in the patient; generating with the computer system, a model of the anatomical ROI from the one or more pre-operative images; acquiring an image of the patient when an optical tracker is arranged on a landmark in the anatomical ROI using an imaging system, wherein the image of the patient depicts at least one of a position or an orientation of the optical tracker relative to the anatomical ROI; generating registered data with the computer system by registering the image of the patient with at least one of the one or more pre-operative images and the model of the anatomical ROI; and displaying the registered data on a display, wherein the registered data comprises a visual depiction of the optical tracker relative to the anatomical ROI in order to provide visual guidance to a user of a placement of a surgical implant or surgical tool relative to the anatomical ROI.

It is another aspect of the present disclosure to provide an optical tracker comprising a base composed of a biocompatible material and extending from a proximal surface to a distal surface along a central axis; and a channel formed in the base and extending from the proximal surface of the base to the distal surface of the base along the central axis, wherein channel is sized and shaped to receive one of a guide pin or a guidewire.

It is another aspect of the present disclosure to provide a kit comprising an optical tracker and a reorientation tool. The optical tracker comprising a base composed of a biocompatible material and extending from a proximal surface to a distal surface along a central axis; and a channel formed in the base and extending from the proximal surface of the base to the distal surface of the base along the central axis, wherein channel is sized and shaped to receive one of a guide pin or a guidewire. The reorientation tool comprising a fiducial part comprising an annular base having a central aperture in which a notch is formed; a key part sized and shaped to be received by the central aperture of the fiducial part, the key part comprising an annular base having a central aperture, wherein a catch is formed on an outer surface of the annular base of the key part, wherein the catch is sized and shaped to operative engage the notch formed in the central aperture of the fiducial part; and one or more interchangeable insert parts, each insert part comprising a cylindrical base that is sized and shaped to be received by the central aperture of the key part, wherein each insert part comprises at least one channel that defines a trajectory having a unique polar angle, wherein each insert part is rotatable within the central aperture of the key part to define a unique azimuthal angle.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for positioning a surgical implant, such as a glenoid component, or other medical device intra-operatively. In general, the systems and methods described in the present disclosure implement a computer vision system, which may be a structured light computer vision system, together with a suitable optical tracker as an accurate intra-operative tool for predicting post-operative implant position in surgical procedures.

As stated, the systems and methods described in the present disclosure enable a surgical guidance system that can be used for accurate placement of a surgical implant. The systems and methods described in the present disclosure can also enable a surgical guidance system that can be used for accurate placement of other implantable medical devices, or for the accurate positioning of a surgical instrument.

The implant or surgical instrument position is generally defined by a start point and trajectory of a guide pin, guidewire, or other landmark, from which the remaining surgical steps proceed. The systems and methods described in the present disclosure provide an intra-operative surgical guidance system that implements an imaging system, such as a structured light sensor and computer vision algorithms, to verify the position of the surgical implant, implantable medical device, or surgical instrument intra-operatively. Once validated, the systems and methods described in the present disclosure can intra-operatively detect instances where the guide pin, guidewire, or other landmark, is malpositioned, enabling surgeons to re-position it prior to preparation and implantation of the surgical implant, or prior to the administration of a therapeutic agent or effect using a surgical instrument.

Figure 1A:
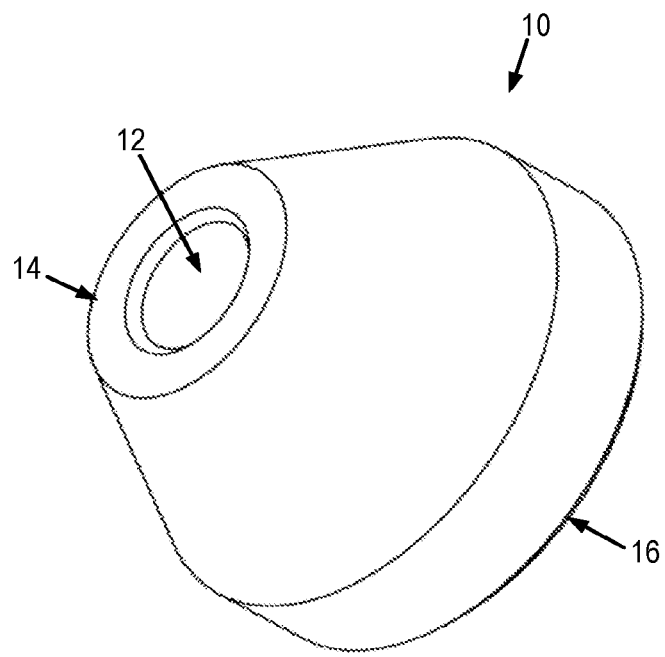
FIGS. 1A and 1B show an example of an optical tracker that can be implemented with the systems and methods described in the present disclosure.
Figure 1B:
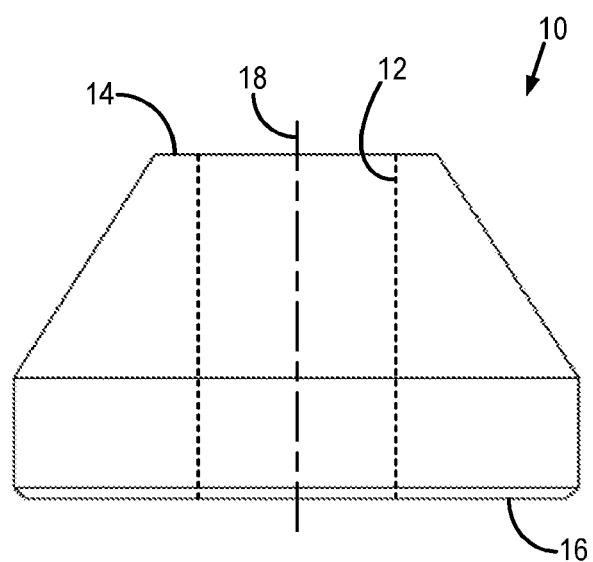

Referring now to FIGS. 1A and 1B, an example of an optical tracker 10 that can be used for accurate guidance and positioning of a surgical implant or other implantable medical device is illustrated. The optical tracker 10 includes a channel 12 extending from a proximal surface 14 to a distal surface 16 of the optical tracker 10 along a central axis 18 of the optical tracker 10. The channel 12 is sized and shaped to receive a guide, which may be a guide wire, a guide pin on a surface of the surgical implant or other medical device to be tracked by the optical tracker 10, or another suitable structure that facilitates guidance of the placement, positioning, or both, of a surgical implant or other medical device. As one example, the channel 12 can have a circular cross section that is sized to receive a guide wire or a guide pin on a glenoid component of a shoulder implant.

The optical tracker 10 is preferably radially symmetric about its central axis 18. Having this radial symmetry reduces the degrees-of-freedom needed for registering images of the optical tracker 10. It will be appreciated by those skilled in the art that the optical tracker 10 does not need to be radially symmetric.

In some embodiments, the optical tracker 10 is shaped such that a leading surface of the optical tracker 10 is chamfered, beveled, or otherwise includes a region where the outer extent of the optical tracker 10 is reduced. As one non-limiting example, the proximal surface 14 of the optical tracker 10 can be chamfered such that the outer diameter of the optical tracker 10 reduces from a first outer diameter to a second outer diameter at the proximal end of the optical tracker 10 that is smaller than the first outer diameter.

As one non-limiting example, the optical tracker 10 can be a radially symmetric annular structure having an outer diameter of 12 mm and a channel 12 having an inner diameter of 3.2 mm, which is sized to receive a Steinman pin used for a central glenoid guide pin.

The optical tracker 10 is generally composed of a biocompatible material. For instance, the optical tracker 10 can be machined or otherwise manufactured from a medical grade polymer, such as medical grade polyether ether ketone (PEEK) meeting the ISO 10993-5 standard for biocompatibility.

In some embodiments, the optical tracker 10 is composed of a biocompatible material that is also sterilizable, such that the optical tracker 10 can be sterilized after use and used again in a different procedure. For instance, the optical tracker 10 can be composed of a biocompatible material that can be sterilized using a steam autoclave or other suitable sterilization process. In some embodiments, the optical tracker 10 can be made to be disposable.

The optical tracker 10 is colored or otherwise designed to be visible to an imaging system, such as an optical surface imaging system. As one example, an optical surface imaging system can include a structured light imaging system. As one example, the optical tracker 10 can be colored such that the optical tracker 10 has sufficient contrast relative to tissues, surgical instruments, and other objects that may be present in the surgical field (e.g., gloves covering a surgeon's hand). As one non-limiting example, for applications where the optical tracker 10 is imaged with a structured light imaging system, the optical tracker 10 can be colored as blue or gray.

As described, the optical tracker 10 is generally constructed to be visible to one or more particular imaging systems. In some instances, the optical tracker 10 can be designed for use with a structured light imaging system. In other instances, the optical tracker 10 can be designed to be visible with other medical imaging modalities, including x-ray imaging and magnetic resonance imaging.

Figure 2A:
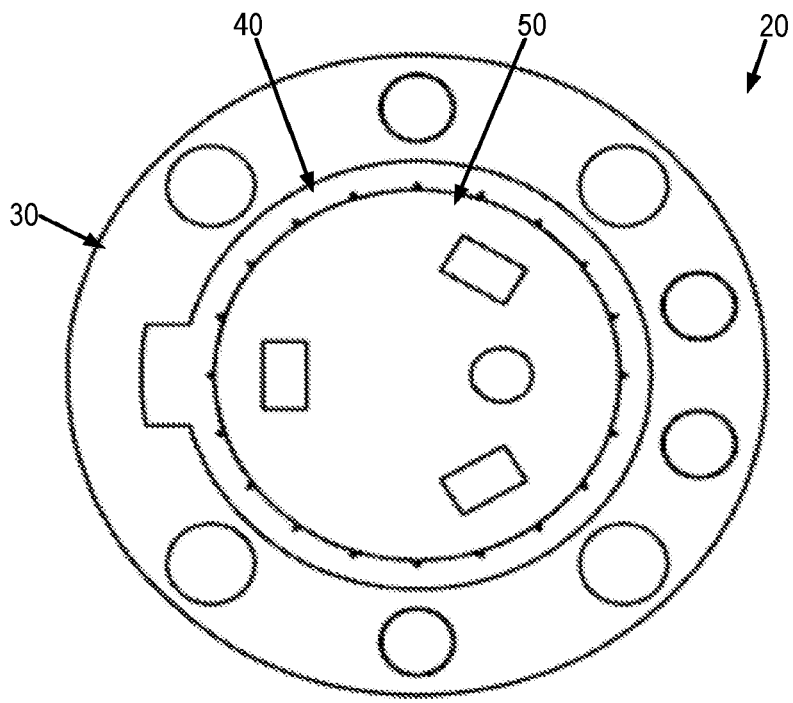
FIGS. 2A and 2B show an example of a reorientation tool that can be implemented with the systems and methods described in the present disclosure.
Figure 2B:
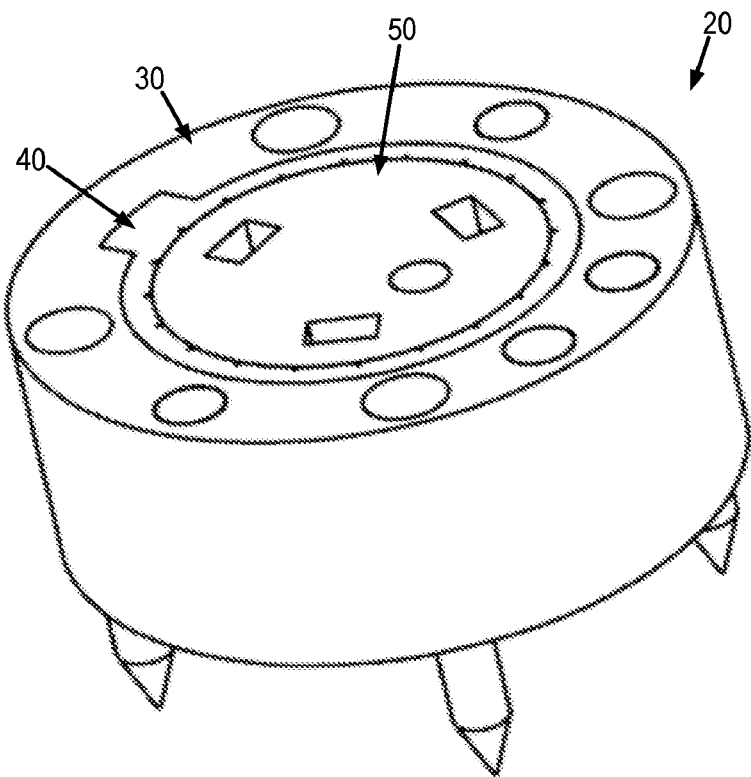

Referring now to FIGS. 2A and 2B, an example of a reorientation tool 20 that can be used to facilitate reorientation of the surgical implant, or other implantable medical device, is shown. The reorientation tool 20 generally includes a fiducial part 30, a key part 40, and an insert part 50. Like the optical tracker 10, the reorientation tool 20 and its constituent parts may be composed of a biocompatible material. In some instances, one or more of the constituent parts of the reorientation tool 20 may be designed to have unique visualization properties to facilitate visualization of the reorientation tool 20 and its constituent parts in one or more images. For instance, the fiducial part 30 can be composed of a material that is colored to be visible in images acquired with a structured light imaging system, and with sufficient contrast relative to the surgical field, the surgical implant, the optical tracker, or combinations thereof.

Figure 3A:
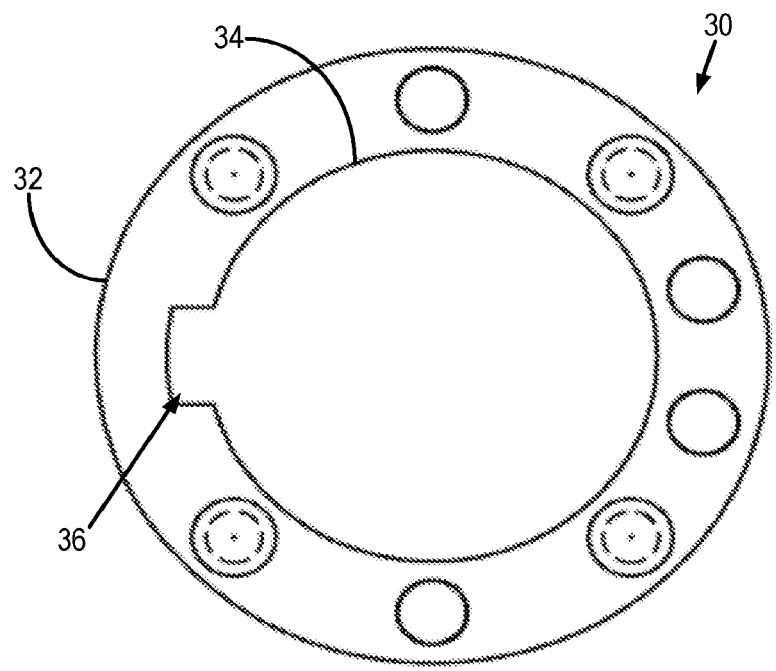
FIGS. 3A and 3B show a fiducial part that forms a part of the reorientation tool shown in FIGS. 2A and 2B.
Figure 3B:
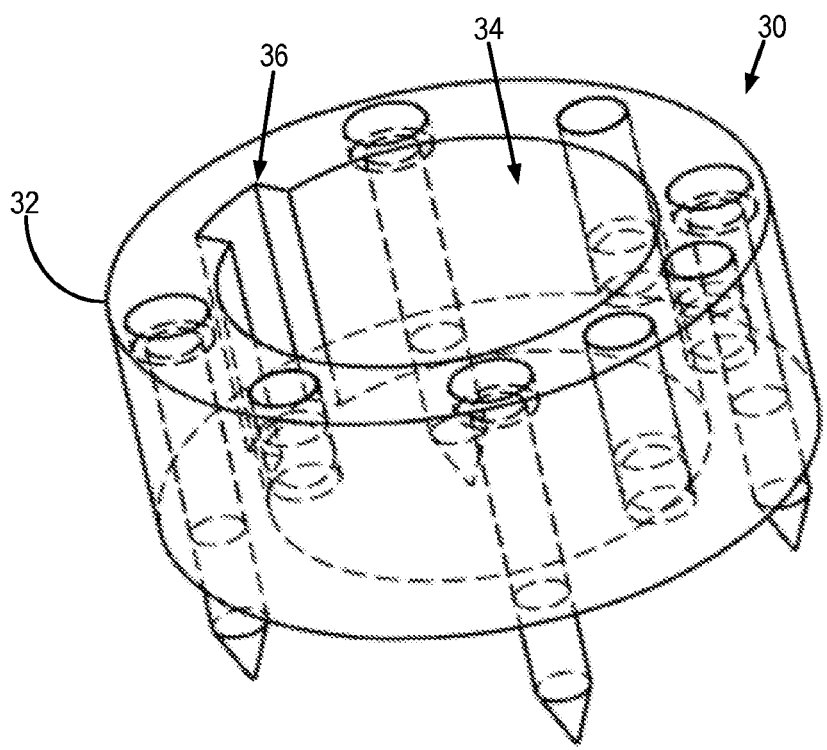

As shown in FIGS. 3A and 3B, the fiducial part 30 of the reorientation tool 20 generally includes an annular base 32 having a central aperture 34 that is sized and shaped to receive the key part 40 of the reorientation tool 20. As shown, the central aperture 34 can have a generally circular cross section; however, the central aperture 34 can also have different cross sectional shapes. The central aperture 34 can have a notch 36 formed therein.

Figure 4A:
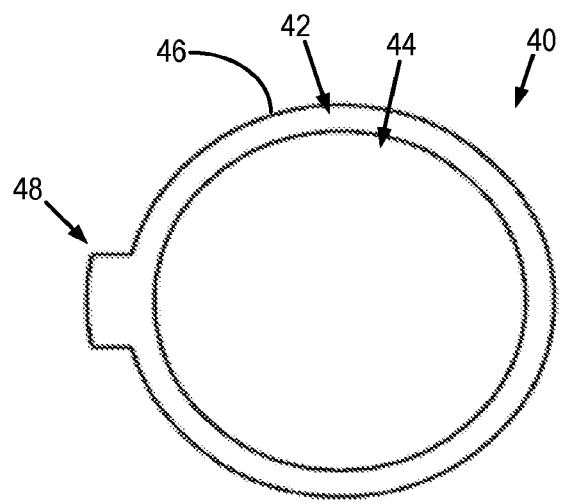
FIGS. 4A and 4B show a key part that forms a part of the reorientation tool shown in FIGS. 2A and 2B.
Figure 4B:
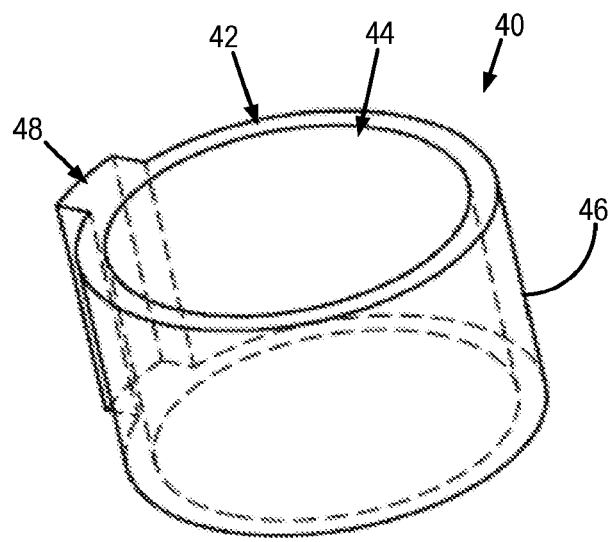

As shown in FIGS. 4A and 4B, the key part 40 of the reorientation tool 20 generally includes an annular base 42 having a central aperture 44 that is sized and shaped to receive the insert part 50. As shown, the central aperture 44 can have a generally circular cross section. The outer surface 46 of the annular base 42 has a catch 48 formed thereon, which is sized and shaped to be received by the notch 36 on the fiducial part 30 when the key part 40 is arranged within the fiducial part 30. Interlocking the catch 48 and notch 36 prevents the key part 40 from rotating within the central aperture 34 of the fiducial part 30.

Figure 5A:
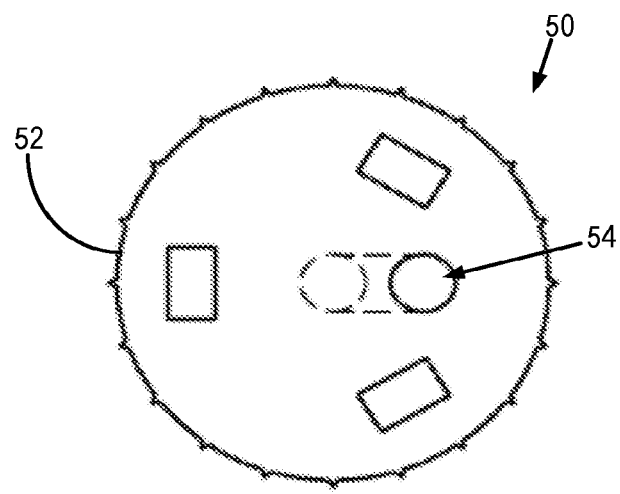
FIGS. 5A and 5B show an interchangeable insert part that forms a part of the reorientation tool shown in FIGS. 2A and 2B.
Figure 5B:
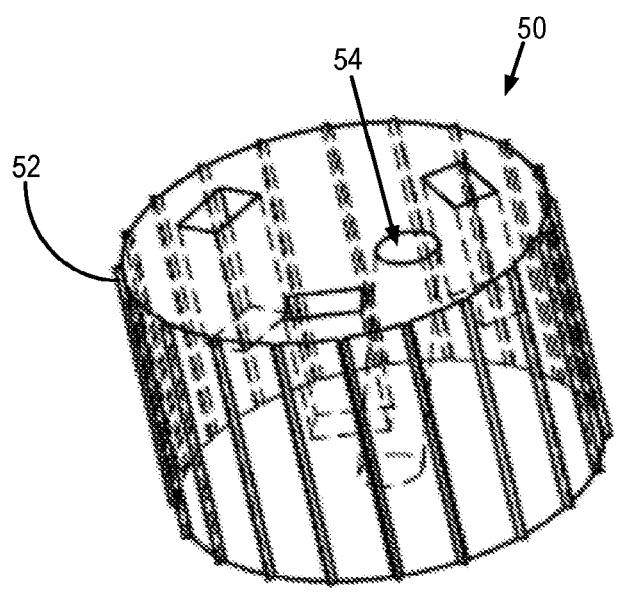

As shown in FIGS. 5A and 5B, the insert part 50 of the reorientation tool 20 generally includes a base 52 that is sized and shaped to be received by the central aperture 44 of the key part 40. The base 52 has formed therein one or more channels 54 that correspond to different trajectories for the guide pin, guidewire, or other landmark, that can be used for guidance of the surgical implant. The different channels 54 therefore define trajectories with different polar angles. The base 52 is rotatable within the central aperture 44 of the key part 40, thereby allowing for the adjustment of the azimuthal angle of the trajectories defined by the one or more channels 54. Different insert parts 50 can be constructed to define different trajectories, such that the insert part 50 can be interchanged during the surgical procedure to achieve the desired trajectory for the surgical implant or other medical device.

Having described an example of an optical tracker and reorientation tool, methods for providing surgical guidance to a user during a surgical procedure using the systems described in the present disclosure are now described.

Figure 6:
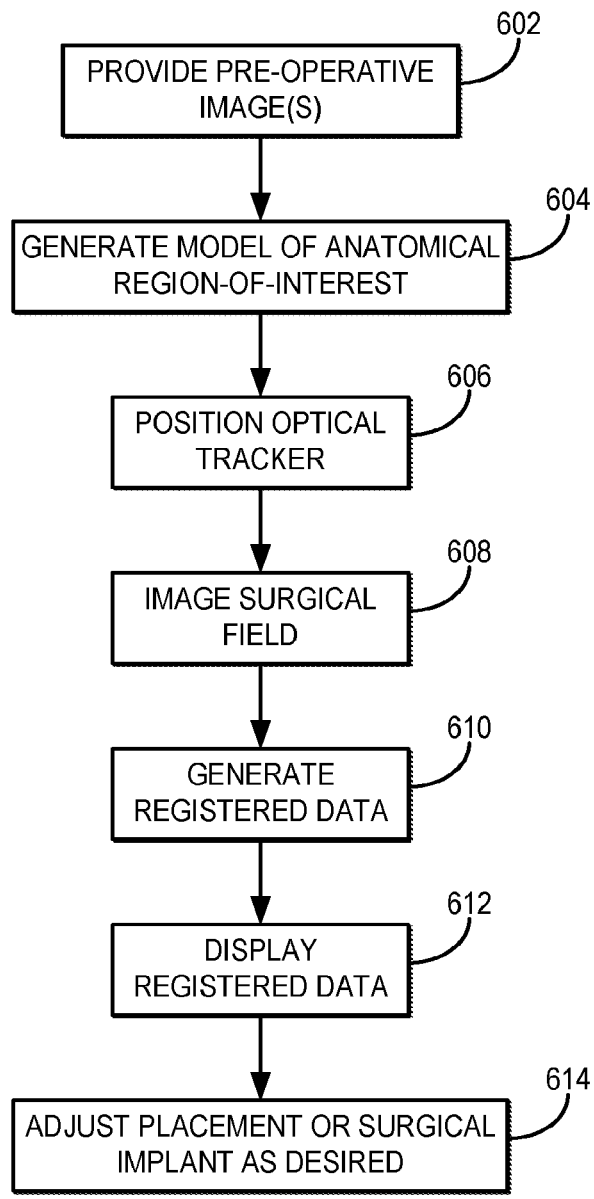
FIG. 6 illustrates a flowchart setting forth the steps of an example method for providing surgical guidance using the systems described in the present disclosure.

Referring now to FIG. 6, a flowchart is illustrated as setting forth the steps of an example method for providing guidance in the positioning of a surgical implant using the systems described in the present disclosure.

The method includes providing pre-operative images of the patient to a computer system, as indicated at step 602. The pre-operative images can be images acquired with an x-ray imaging system, which may include a computed tomography ("CT") imaging system, images acquired with a magnetic resonance imaging ("MRI") system, images acquired with other suitable medical imaging systems, or combinations thereof. The pre-operative images can be provided to the computer system by accessing or otherwise retrieving previously acquired images from a memory or other suitable data storage, or can include acquiring the images with a medical imaging system and communicating the images from the medical imaging system to the computer system.

A model of the anatomical region-of-interest (e.g., the region where the surgical implant will be placed) is generated from the pre-operative images, as indicated at step 604. Alternatively, the model can be a previously generated model that is provided to the computer system. The model may be, for example, a three-dimensional model of the anatomical region-of-interest. In some instances, the model can include a model of one or more anatomical structures in the anatomical region-of-interest. As one non-limiting example, the model can be of a patient's scapula.

During placement of the surgical implant, or other medical device, a guidewire is typically used to provide guidance and accurate positioning of the surgical implant or other medical device. An optical tracker, such as those described in the present disclosure, can be positioned over such a guidewire, as indicated at step 606. Alternatively, the optical tracker can be positioned on a guide pin or other suitable structure on the surgical implant or medical device.

When the surgical implant is in place with the optical tracker, an image of the surgical field is then obtained, as indicated at step 608. As one example, the image of the surgical field can be obtained using a structured light imaging system. Alternatively, other imaging systems can be used, included optical imaging systems. When a structured light imaging system is used, the image may include a three-dimensional point cloud representative of a surface topology of the surgical field. Additionally or alternatively, when a structured light imaging system is used, the image may include a three-dimensional point cloud representative of a surface topology and associated spectral properties (e.g., color, brightness) of the surgical field. The image may also include a mesh representation of the surface topology, such as a polygon mesh where vertices, edges, and faces define the surface topology and associated spectral properties.

As one example, the image of the surgical field can be obtained using a structured light imaging system such as Einscan Pro hand-held structured light scanner (Shining 3D, Hangzhou, China). This device acquires a three-dimensional color image of the target anatomy by projecting patterned optical light on the target and acquiring and processing binocular color images of the illuminated target. The imaging system can, in general, be offset from the surgical field to permit image acquisition without violating the sterility of the surgical field. As an example, the imaging system can be offset by 400 mm.

Registered data are produced by registering the image of the surgical field with the pre-operative images, the model of the anatomic region-of-interest, or both, as indicated at step 610. In this manner, the optical tracker, visible in the image of the surgical field, can be registered with the anatomic region-of-interest. The registered data generally include information pertaining to the mechanical relationship between the optical tracker and the surgical implant or surgical tool to which the optical tracker was mechanically coupled during imaging, or to which the surgical implant or surgical tool is mechanically coupled after the optical tracker has been imaged. As a result, when the image depicting the optical tracker is registered to the pre-operative images, the model of the anatomical region-of-interest, or both, information about that mechanical relationship is registered with the anatomical region-of-interest. Then, based on that mechanical relationship being registered with the target anatomy, the spatial relationship of the surgical implant or surgical tool is defined relative to the anatomical region-of-interest. For example, the spatial relationship between the surgical implant or tool with respect to the anatomical region-of-interest can be calculated using the registered data and based on the mechanical relationship between the optical tracker and the surgical implant or tool. In these instances, the calculated spatial relationship can be stored with the other registered data, or separately.

In general, surface-to-surface registration of the target anatomy (e.g., the anatomical region-of-interest) from an optical surface image to a model derived from pre-operative imaging can be improved when the optical surface of the target anatomical be accurately determined from the pre-operative image. When the target anatomy is a joint, such as the shoulder, the surface of the joint visible to the intra-operative optical surface imaging system is composed of soft tissues such as articular cartilage and fibrocartilage. These soft tissues are present in all healthy shoulders, but may be degraded to a greater or lesser extent in the setting of joint degeneration (e.g., arthritis).

In some examples, the surface of the target anatomy can be accurately modeled by segmenting and modeling the target anatomy surface, including any remaining soft tissues (e.g., articular cartilage and fibrocartilage), from pre-operative imaging that resolves these structures (e.g., MRI, MRI arthrography, or CT arthrography).

In some other examples, the surface of the target anatomy can be accurately modeled by mechanically or chemically debrided soft tissues prior to obtaining the intra-operative optical surface image. In this way, the subchondral bone would be visualized directly in the optical surface image, such that the pre-operative target anatomy model could be derived from segmentation and modeling the bone of the target anatomy. This would facilitate use of pre-operative imaging systems (e.g., CT) that may not otherwise accurately resolve articular soft tissue structures.

In some other examples, the surface of the target anatomy can be accurately modeled by processing the pre-operative images obtained from an imaging system (e.g., CT) that does not accurately resolve these soft tissue structures. As an example, this image processing can include enhancing the pre-operative images so that the soft tissue structures could be resolved and directly modeled. Additionally or alternatively, this image processing could include inferring the volumes of soft tissue structures based on the shape and relationship of visualized structures, such as bone and the joint space. Additionally or alternatively, the shape of the articular surface could be inferred from the pre-operative images using machine learning techniques.

The registered data can be displayed to a user, as indicated at step 612. For instance, the registered data can include one or more display elements that are generated and displayed as overlays with the pre-operative images, the model of the anatomic region-of-interest, or both. The display elements can depict the position, orientation, or both, of the optical tracker, the surgical implant (or other medical device), the guidewire, or combinations thereof. In some instances, the registered data can also include data representative of an accuracy of the position, orientation, or both, of the surgical implant or other medical device. Based on feedback from these data, the surgeon can fine tune or otherwise adjust the position, orientation, or both of the surgical implant or other medical device, as indicated at step 614. In some instance, the reorientation tool described in the present disclosure can be used to facilitate this adjustment.

As an example, the systems and methods described in the present disclosure can be implemented for evaluating the position of the central glenoid pin intra-operatively during total shoulder arthroplasty, in which this guide pin is used to prepare the glenoid for implantation of the glenoid component. In this way, evaluating the position of the central glenoid pin can determine the orientation of the glenoid component relative to the subject's anatomy (e.g., the scapula). When the central glenoid guide pin is placed, an optical tracker is placed over the guide pin. A structured light imaging system, which may include a hand-held structured light sensor, can then be used to obtain a topographical optical image of the exposed glenoid surface.

Figure 7:
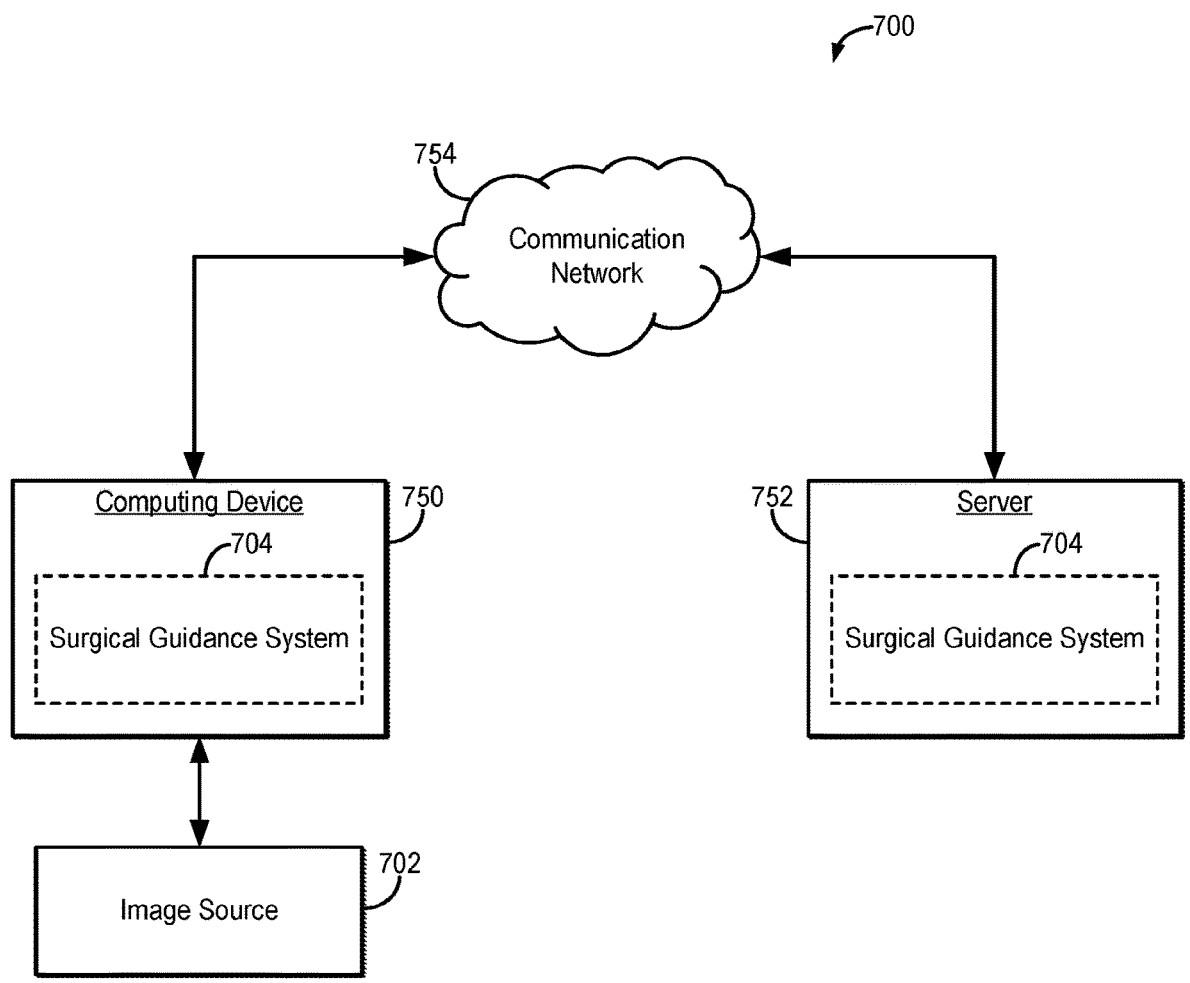
FIG. 7 is a block diagram of an example system that can implement the methods described in the present disclosure.

Referring now to FIG. 7, an example of a computer vision system 700 for generating providing guidance during a surgical procedure (e.g., when implanting a surgical implant or other implantable medical device) in accordance with some embodiments of the systems and methods described in the present disclosure is shown. The computer vision system 700 displays the three-dimensional position of the guide pin, guidewire, or other landmark, which guides the surgical implant preparation and determines the placement (e.g., the version, inclination, and/or offset) of the surgical implant. The position of the guide pin, guidewire, or other landmark, is displayed with respect to one or more pre-operative images, and optionally a pre-operative plan. The position of the guide pin, guidewire, or other landmark, is registered from the topographical optical image of the surgical field, which includes the anatomy of interest (e.g., the glenoid surface) and the optical tracker centered at the guide pin, guidewire, or other landmark. The optical tracker and anatomy of interest are segmented and registered in the reference frame of this single surface image.

As shown in FIG. 7, a computing device 750 can receive one or more types of image data from image source 702. In some embodiments, computing device 750 can execute at least a portion of a surgical guidance system 704 to generate registered data for guiding a surgical implant or otherwise verifying a position, orientation, or placement of a surgical implant from image data received from the image source 702.

Additionally or alternatively, in some embodiments, the computing device 750 can communicate information about image data received from the image source 702 to a server 752 over a communication network 754, which can execute at least a portion of the surgical guidance system 704 to generate registered data for guiding a surgical implant or otherwise verifying a position, orientation, or placement of a surgical implant from image data received from the image source 702. In such embodiments, the server 752 can return information to the computing device 750 (and/or any other suitable computing device) indicative of an output of the surgical guidance system 704 to generate registered data for guiding a surgical implant or otherwise verifying a position, orientation, or placement of a surgical implant from image data received from the image source 702.

In some embodiments, computing device 750 and/or server 752 can be any suitable computing device or combination of devices, such as a desktop computer, a laptop computer, a smartphone, a tablet computer, a wearable computer, a server computer, a virtual machine being executed by a physical computing device, and so on. As described above, the surgical guidance system 704 can register image data with pre-operative images to generate registered data. The computing device 750 and/or server 752 can also reconstruct or otherwise images from the image data.

In some embodiments, image source 702 can be any suitable source of image data, such as a structured light image system, an optical imaging system, an x-ray computed tomography system, a magnetic resonance imaging system, another computing device (e.g., a server storing image data), and so on. In some embodiments, image source 702 can be local to computing device 750. For example, image source 702 can be incorporated with computing device 750 (e.g., computing device 750 can be configured as part of a device for capturing, scanning, and/or storing images). As another example, image source 702 can be connected to computing device 750 by a cable, a direct wireless link, and so on. Additionally or alternatively, in some embodiments, image source 702 can be located locally and/or remotely from computing device 750, and can communicate image data to computing device 750 (and/or server 752) via a communication network (e.g., communication network 754).

In some embodiments, communication network 754 can be any suitable communication network or combination of communication networks. For example, communication network 754 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CD MA, GSM, LTE, LTE Advanced, WiMAX, etc.), a wired network, etc. In some embodiments, communication network 754 can be a local area network, a wide area network, a public network (e.g., the Internet), a private or semi-private network (e.g., a corporate or university intranet), any other suitable type of network, or any suitable combination of networks. Communications links shown in FIG. 7 can each be any suitable communications link or combination of communications links, such as wired links, fiber optic links, Wi-Fi links, Bluetooth links, cellular links, and so on.

Figure 8:
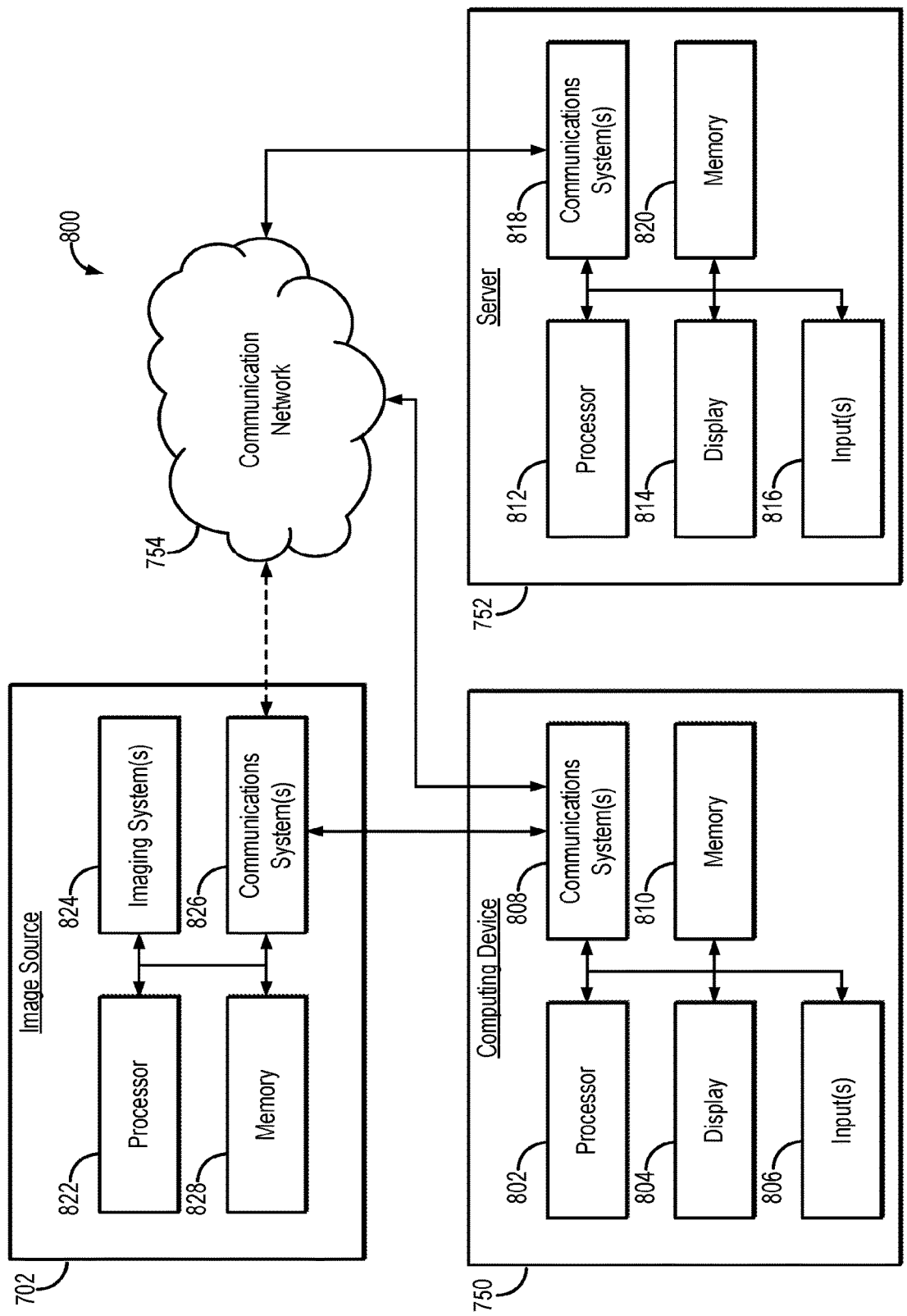
FIG. 8 is a block diagram of example hardware that can implement the system of FIG. 7.

Referring now to FIG. 8, an example of hardware 800 that can be used to implement image source 702, computing device 750, and server 754 in accordance with some embodiments of the systems and methods described in the present disclosure is shown. As shown in FIG. 8, in some embodiments, computing device 750 can include a processor 802, a display 804, one or more inputs 806, one or more communication systems 808, and/or memory 810. In some embodiments, processor 802 can be any suitable hardware processor or combination of processors, such as a central processing unit ("CPU"), a graphics processing unit ("GPU"), and so on. In some embodiments, display 804 can include any suitable display devices, such as a computer monitor, a touchscreen, a television, and so on. In some embodiments, inputs 806 can include any suitable input devices and/or sensors that can be used to receive user input, such as a keyboard, a mouse, a touchscreen, a microphone, and so on.

In some embodiments, communications systems 808 can include any suitable hardware, firmware, and/or software for communicating information over communication network 754 and/or any other suitable communication networks. For example, communications systems 808 can include one or more transceivers, one or more communication chips and/or chip sets, and so on. In a more particular example, communications systems 808 can include hardware, firmware and/or software that can be used to establish a Wi-Fi connection, a Bluetooth connection, a cellular connection, an Ethernet connection, and so on.

In some embodiments, memory 810 can include any suitable storage device or devices that can be used to store instructions, values, etc., that can be used, for example, by processor 802 to present content using display 804, to communicate with server 752 via communications system(s) 808, etc. Memory 810 can include any suitable volatile memory, non-volatile memory, storage, or any suitable combination thereof. For example, memory 810 can include RAM, ROM, EEPROM, one or more flash drives, one or more hard disks, one or more solid state drives, one or more optical drives, etc. In some embodiments, memory 810 can have encoded thereon a computer program for controlling operation of computing device 750. In such embodiments, processor 802 can execute at least a portion of the computer program to present content (e.g., ultrasound images, user interfaces, graphics, tables, etc.), receive content from server 752, transmit information to server 752, etc.

In some embodiments, server 752 can include a processor 812, a display 814, one or more inputs 816, one or more communications systems 818, and/or memory 820. In some embodiments, processor 812 can be any suitable hardware processor or combination of processors, such as a CPU, a GPU, etc. In some embodiments, display 814 can include any suitable display devices, such as a computer monitor, a touchscreen, a television, etc. In some embodiments, inputs 816 can include any suitable input devices and/or sensors that can be used to receive user input, such as a keyboard, a mouse, a touchscreen, a microphone, etc.

In some embodiments, communications systems 818 can include any suitable hardware, firmware, and/or software for communicating information over communication network 754 and/or any other suitable communication networks. For example, communications systems 818 can include one or more transceivers, one or more communication chips and/or chip sets, etc. In a more particular example, communications systems 818 can include hardware, firmware and/or software that can be used to establish a Wi-Fi connection, a Bluetooth connection, a cellular connection, an Ethernet connection, etc.

In some embodiments, memory 820 can include any suitable storage device or devices that can be used to store instructions, values, etc., that can be used, for example, by processor 812 to present content using display 814, to communicate with one or more computing devices 750, etc. Memory 820 can include any suitable volatile memory, non-volatile memory, storage, or any suitable combination thereof. For example, memory 820 can include RAM, ROM, EEPROM, one or more flash drives, one or more hard disks, one or more solid state drives, one or more optical drives, etc. In some embodiments, memory 820 can have encoded thereon a server program for controlling operation of server 752. In such embodiments, processor 812 can execute at least a portion of the server program to transmit information and/or content (e.g., generated additional ultrasound data, ultrasound images, a user interface, etc.) to one or more computing devices 750, receive information and/or content from one or more computing devices 750, receive instructions from one or more devices (e.g., a personal computer, a laptop computer, a tablet computer, a smartphone, etc.), etc.

In some embodiments, image source 702 can include a processor 822, an imaging system 824, one or more communications systems 826, and/or memory 828. In some embodiments, processor 822 can be any suitable hardware processor or combination of processors, such as a CPU, a GPU, etc. In some embodiments, imaging system 824 can be any suitable imaging system configured to acquire images. As one example, the imaging system 824 can be a structured light imaging system. Additionally or alternatively, in some embodiments, imaging system 824 can include any suitable hardware, firmware, and/or software for coupling to and/or controlling operations of an imaging system. In some embodiments, one or more portions of imaging system 824 can be removable and/or replaceable.

Note that, although not shown, image source 702 can include any suitable inputs and/or outputs. For example, image source 702 can include input devices and/or sensors that can be used to receive user input, such as a keyboard, a mouse, a touchscreen, a microphone, a trackpad, a trackball, etc. As another example, image source 702 can include any suitable display devices, such as a computer monitor, a touchscreen, a television, etc., one or more speakers, etc.

In some embodiments, communications systems 826 can include any suitable hardware, firmware, and/or software for communicating information to computing device 750 (and, in some embodiments, over communication network 754 and/or any other suitable communication networks). For example, communications systems 826 can include one or more transceivers, one or more communication chips and/or chip sets, etc. In a more particular example, communications systems 826 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, etc.

In some embodiments, memory 828 can include any suitable storage device or devices that can be used to store instructions, values, image data, etc., that can be used, for example, by processor 822 to control imaging system 824, and/or receive image data from imaging system 824; to generate images from data, generated registered data, or combinations thereof; present content (e.g., images, registered data, display elements, a user interface, etc.) using a display; communicate with one or more computing devices 750; and so on. Memory 828 can include any suitable volatile memory, non-volatile memory, storage, or any suitable combination thereof. For example, memory 828 can include RAM, ROM, EEPROM, one or more flash drives, one or more hard disks, one or more solid state drives, one or more optical drives, etc. In some embodiments, memory 828 can have encoded thereon a program for controlling operation of image source 702. In such embodiments, processor 822 can execute at least a portion of the program to generate images, transmit information and/or content (e.g., data) to one or more computing devices 750, receive information and/or content from one or more computing devices 750, receive instructions from one or more devices (e.g., a personal computer, a laptop computer, a tablet computer, a smartphone, etc.), etc.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A kit, comprising:
an optical tracker comprising:
a base composed of a biocompatible material and extending from a proximal surface to a distal surface along a central axis;
a channel formed in the base and extending from the proximal surface of the base to the distal surface of the base along the central axis, wherein channel is sized and shaped to receive one of a guide pin or a guidewire;
a reorientation tool comprising:
a fiducial part comprising:
an annular base having a central aperture;
a notch formed as a recessed portion of an inner surface of the central aperture of the fiducial part;
a key part comprising:
an annular base having a central aperture, wherein the annular base of the key part is sized and shaped to be received by the central aperture of the fiducial part;
a catch formed as a raised portion on an outer surface of the annular base of the key part, wherein the catch is sized and shaped to be received by the notch formed in the central aperture of the fiducial part such that the catch interlocks with the notch to prevent the key part from rotating within the central aperture of the fiducial part;
one or more interchangeable insert parts, each insert part comprising a cylindrical base that is sized and shaped to be received by the central aperture of the key part, wherein each insert part comprises at least one channel that defines a trajectory having a unique polar angle, wherein each insert part is rotatable within the central aperture of the key part to define a unique azimuthal angle.

2. The kit as recited in claim 1, wherein the biocompatible material of the base of the optical tracker is colored in order to provide visual contrast with a surgical field in an image acquired with a structured light imaging system.

3. The kit as recited in claim 1, wherein the base of the optical tracker comprises a first portion having a first outer diameter and a second portion that tapers from the first outer diameter to a second outer diameter that is smaller than the first outer diameter.

4. The kit as recited in claim 1, wherein the base of the optical tracker is radially symmetric about the central axis.

5. The kit as recited in claim 2, wherein the biocompatible material of the base is colored at least one of gray or blue in order to provide the visual contrast with the surgical field.

6. The kit as recited in claim 3, wherein the second portion of the base defines a leading surface of the optical tracker.

7. A reorientation tool for reorienting a surgical implant, comprising:
a fiducial part comprising:
an annular base having a central aperture;
a notch formed as a recessed portion of an inner surface of the central aperture of the fiducial part;
a key part comprising:
an annular base having a central aperture, wherein an outer diameter of the annular base of the key part is sized and shaped to be received by the central aperture of the fiducial part;
a catch formed as a raised portion extending beyond the outer diameter of the annular base of the key part, wherein the catch is sized and shaped to be received by the notch formed in the central aperture of the fiducial part such that when the catch is received by and interlocked with the notch the key part cannot rotate relative to the central aperture of the fiducial part;
an insert part comprising:
a cylindrical base having an outer diameter that is sized and shaped to be received by the central aperture of the key part;
a channel formed in the cylindrical base, wherein the channel defines a trajectory having a unique polar angle,
wherein the insert part is rotatable within the central aperture of the key part to define a unique azimuthal angle.

* * * * *